(12) United States Patent
Nagayasu et al.

(10) Patent No.: US 9,713,807 B2
(45) Date of Patent: Jul. 25, 2017

(54) METHOD FOR PRODUCING HYDROISOMERIZATION CATALYST AND METHOD FOR PRODUCING LUBRICANT BASE OIL

(71) Applicant: JX NIPPON OIL & ENERGY CORPORATION, Tokyo (JP)

(72) Inventors: Yoshiyuki Nagayasu, Tokyo (JP); Kazuaki Hayasaka, Tokyo (JP); Marie Iwama, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 221 days.

(21) Appl. No.: 14/388,945

(22) PCT Filed: Mar. 29, 2013

(86) PCT No.: PCT/JP2013/059660
§ 371 (c)(1),
(2) Date: Sep. 29, 2014

(87) PCT Pub. No.: WO2013/147219
PCT Pub. Date: Oct. 3, 2013

(65) Prior Publication Data
US 2015/0051432 A1 Feb. 19, 2015

(30) Foreign Application Priority Data
Mar. 30, 2012 (JP) .................. 2012-082501

(51) Int. Cl.
*C07C 5/27* (2006.01)
*B01J 29/74* (2006.01)
(Continued)

(52) U.S. Cl.
CPC ......... *B01J 29/7484* (2013.01); *B01J 29/076* (2013.01); *B01J 29/703* (2013.01);
(Continued)

(58) Field of Classification Search
CPC .................................... C07C 5/2791
See application file for complete search history.

(56) References Cited

U.S. PATENT DOCUMENTS 5,282,958 A    2/1994    Santilli et al.
5,817,907 A * 10/1998    Benazzi .................. B01J 29/65
                                                    585/671
(Continued)

FOREIGN PATENT DOCUMENTS

CN    102333592    1/2012
JP    07-157774    6/1995
(Continued)

OTHER PUBLICATIONS

Notice of Allowance issued in Korean Counterpart Application No. 10-2014-7029254, dated May 10, 2016.
(Continued)

*Primary Examiner* — In Suk Bullock
*Assistant Examiner* — Youngsul Jeong
(74) *Attorney, Agent, or Firm* — Greenblum & Bernstein, P.L.C.

(57) ABSTRACT

A method for producing a hydroisomerization catalyst according to the present invention includes: a first step of preparing a catalyst to be treated, which contains a support having a one-dimensional porous structure including a 10-membered ring and at least one metal selected from the group consisting of: group 8 to 10 metals of the periodic table, Mo, and W supported on the hydroisomerization catalyst; and a second step of producing a hydroisomerization catalyst having a carbon content of 0.4 to 2.5% by mass by subjecting the catalyst to be treated to a coking treatment by means of a carbon-containing compound.

8 Claims, 1 Drawing Sheet

(51) Int. Cl.
*C10G 45/62* (2006.01)
*C10G 45/64* (2006.01)
*B01J 29/076* (2006.01)
*B01J 29/78* (2006.01)
*B01J 29/70* (2006.01)

(52) U.S. Cl.
CPC ........... *B01J 29/74* (2013.01); *B01J 29/7461* (2013.01); *B01J 29/78* (2013.01); *B01J 29/7861* (2013.01); *B01J 29/7884* (2013.01); *B01J 29/7892* (2013.01); *C07C 5/2791* (2013.01); *C10G 45/62* (2013.01); *C10G 45/64* (2013.01); *B01J 2229/186* (2013.01)

(56) References Cited

U.S. PATENT DOCUMENTS

| | | | |
|---|---|---|---|
| 6,569,312 | B1 | 5/2003 | Carroll et al. |
| 8,758,596 | B2 | 6/2014 | Hayasaka et al. |
| 2005/0277800 | A1* | 12/2005 | Sugi .................. B01J 29/7057 585/739 |
| 2011/0270010 | A1 | 11/2011 | Hayasaka et al. |
| 2013/0008827 | A1* | 1/2013 | Nagayasu ............ B01J 29/7461 208/64 |

FOREIGN PATENT DOCUMENTS

| | | | |
|---|---|---|---|
| JP | 2004-514019 | | 5/2004 |
| JP | 2010-155187 | | 7/2010 |
| JP | WO 2011122446 | A1 * | 10/2011 .......... B01J 29/7461 |
| JP | 2012-213712 | | 11/2012 |
| WO | 2009/099111 | | 8/2009 |
| WO | 2010/074215 | | 7/2010 |
| WO | 2011/122446 | | 10/2011 |

OTHER PUBLICATIONS

Huybrechts et al., "Bifunctional catalytic isomerization of decane over MTT-type aluminosilicate zeolite crystals with siliceous rim," *Journal of Catalysis*, vol. 239, pp. 451-459, 2006.

Zhao et al., "Synthesis of ZSM-48, zeolites and their catalytic performance in C4-olefin cracking reactions," *Applied Catalysis A: General*, vol. 29, pp. 167-174, 2006.

International Search Report of Patent Application No. PCT/JP2013/059660, mailed Jun. 18, 2013.

English translation of International Preliminary Report on Patentability for PCT/JP2013/059660, which was mailed on Oct. 9, 2014.

Office Action issued in China Counterpart Patent Appl. No. 201380028108.5, dated Oct. 16, 2015.

M Guisnet, ""Coke" molecules trapped in the micropores of zeolites as active species in hydrocarbon transformations", Journal of Molecular Catalysis A: Chemical 182-183, 2002, pp. 367-382.

Huang Xiaohong et al., "Coke-Deposition on MCM-22 Molecular Sieve Catalyst During Isomerization of 1-Butene", Petrochemical Technology, vol. 35, 2006, pp. 314-318.

Chinese Office Action issued with respect to Application No. 201380028108.5, mail date is Aug. 16, 2016.

* cited by examiner

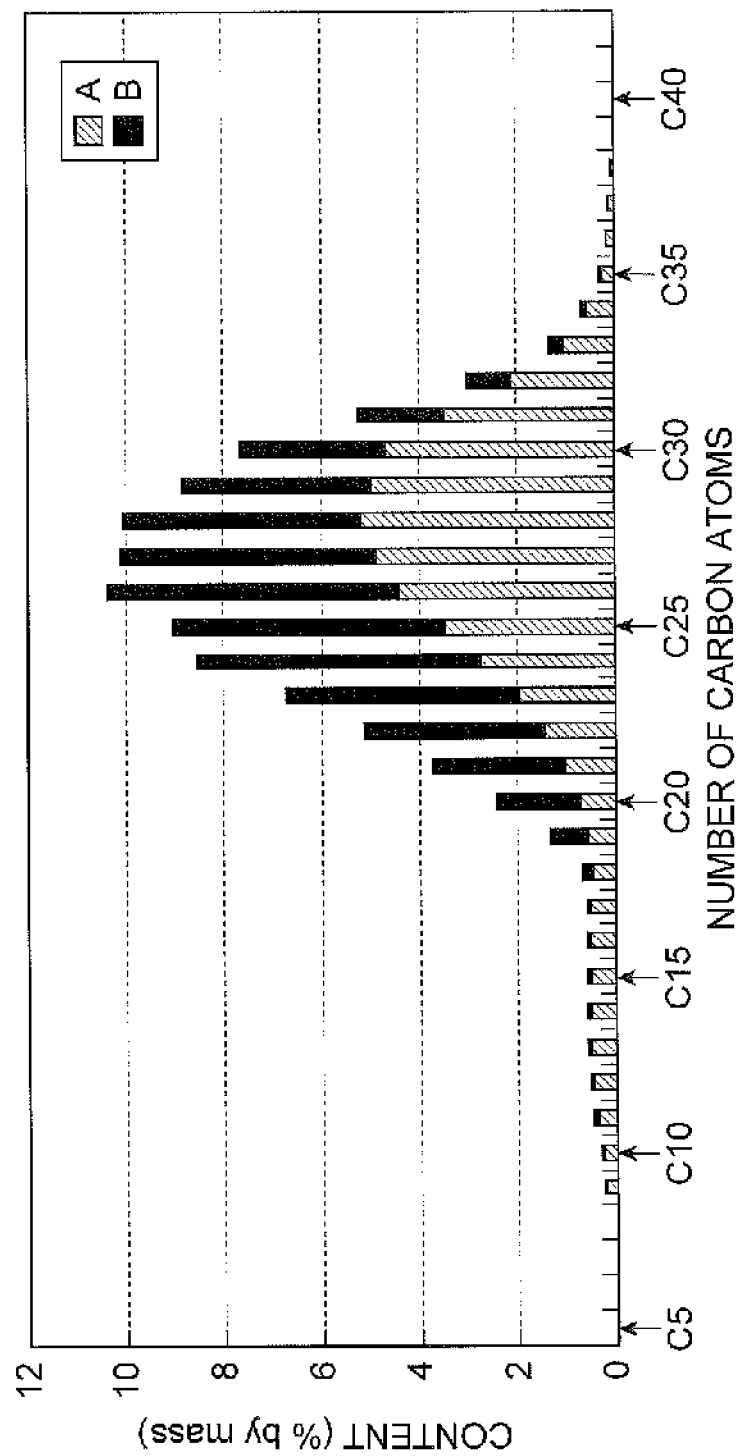

METHOD FOR PRODUCING HYDROISOMERIZATION CATALYST AND METHOD FOR PRODUCING LUBRICANT BASE OIL

TECHNICAL FIELD

The present invention relates to a hydroisomerization catalyst and a method for producing the same. In addition, the present invention relates to a method for producing lubricant base oil using the hydroisomerization catalyst.

BACKGROUND ART

Among petroleum products, for example, lubricants, light gas oils, jet fuels, and the like are products that the cold flow property is considered to be important. Therefore, it is required that wax components, such as normal paraffin, which may degrade the low-temperature fluidity, and isoparaffin, which has a few branches, are entirely or partially eliminated from base oil used in such products, or that such wax components are converted into components other than wax components. In recent years, hydrocarbons prepared by the Fischer Tropsch synthetic process (hereinafter simply referred to as "FT synthetic oil") has attracted attention as feedstock used in producing lubricants or fuels because FT synthetic oil contains no environmental burden-substance, such as sulfur compounds, however, such hydrocarbons contain a large content of wax components.

As a dewaxing technique for eliminating wax components from hydrocarbon oil, a method for extracting wax components by means of a solvent, such as liquefied propane or methyl ethyl ketone (MEK), has been known. However, in addition to requiring high costs, the following problems may arise in this method, such that the type of applicable feedstock is limited, and that the product yield is restricted by the type of the feedstock.

On the other hand, as a dewaxing technique for converting wax components contained in hydrocarbon oil into non-wax components, catalytic dewaxing has been known, for example, in which hydrocarbon oil is contacted with a catalyst known as a bifunctional catalyst, which has a hydrogenation-dehydrogenation function and an isomerization function, in the presence of hydrogen to isomerize normal paraffin contained in hydrocarbon into isoparaffin. As a bifunctional catalyst used in catalytic dewaxing, a catalyst containing molecular sieves including solid acids, particularly zeolites, and group 8 to 10 or group 6 metals of the periodic table has been known, and in particular, a catalyst in which the above-described metal is supported on the molecular sieve has been known.

Catalytic dewaxing is effective as a method for improving the low-temperature fluidity of hydrocarbon oil, and it is necessary to achieve a sufficiently high degree of conversion of normal paraffins in order to produce a fraction applicable as lubricant base oil and fuel base oil. However, the above-described catalyst used in catalytic dewaxing has a hydrocarbon cracking function in addition to an isomerization function, and therefore, in catalytic-dewaxing hydrocarbon oil, lightening of hydrocarbon oil may develop as the degree of conversion of normal paraffins rises, which makes it difficult to efficiently produce desired fractions. In particular, in producing high-quality lubricant base oil for which high viscosity index and low pour point are required, it is very difficult to economically produce a fraction to be prepared by catalytic-dewaxing hydrocarbon oil, and accordingly, synthetic base oils, such as poly-α-olefins, have often been used in the field concerned.

However, in recent years, in the field of producing lubricant base oil and fuel base oil, particularly in the field of producing lubricant base oil, production of group II, group III, and group III+ base oil, which are classified as grades of lubricants specified by the American Petroleum Institute (API), using hydroprocessing has become more and more widespread. Under these circumstances, in order to achieve a desired isoparaffin fraction from hydrocarbon oil including wax components with a high yield, a catalyst having an inhibited cracking activity and a high isomerization reaction activity on hydrocarbons, i.e., a hydroisomerization catalyst having an excellent isomerization selectivity, is required.

Attempts have been made to improve the isomerization selectivity of a catalyst used in catalytic dewaxing. For example, the following Patent Literature 1 discloses a process for producing a dewaxed lubricant, in which a straight-chain hydrocarbon raw material or a hydrocarbon raw material having a few branches having 10 or more carbon atoms is contacted, under an isomerization condition, with a catalyst which includes molecular sieves containing group 8 metals of the periodic table and having middle-size one-dimensional pores, the dimension of crystallite of which not exceeding 0.5μ, i.e., molecular sieves such as ZSM-22, ZSM-23, ZSM-48, and the like.

Note that a zeolite constituting a hydroisomerization catalyst is produced by hydrothermal synthesis in the presence of an organic compound known as "organic template", which usually includes an amino group, ammonium group, and the like, to construct a predetermined pore structure. The synthesized zeolite is calcined at the temperature of 550° C. or higher, for example, in an atmosphere containing molecular oxygen to eliminate organic templates contained therein, as discussed in the final paragraph of "Item 2.1. Materials", page 453 of the following Non Patent Literature 1. Typically, the calcined zeolite is then ion-exchanged to become an ammonium type zeolite in an aqueous solution containing ammonium ions, for example, as described in "Item 2.3. Catalytic experiments", page 453 of the following Non Patent Literature 1. The ion-exchanged zeolite further carries group 8 to 10 metal components of the periodic table. The zeolite carrying the metal component is then charged into a reactor after being dried and having undergone steps such as extruding, and the like if necessary, and typically be calcined at a temperature of about 400° C. in an atmosphere containing molecular oxygen, and further undergoes reduction at a similar temperature by means of hydrogen and the like; thus a catalyst activity of a bifunctional catalyst is impaired.

In a recently proposed method, in order to further improve the isomerization selectivity of a hydroisomerization catalyst, a hydrothermally synthesized zeolite is ion-exchanged in a state in which organic templates are contained, instead of calcining such zeolite at the above-described high temperature, to produce a hydroisomerization catalyst based on the ion-exchanged zeolite (see the following Patent Literature 2, for example).

CITATION LIST

Patent Literature

Patent Literature 1: U.S. Pat. No. 5,282,958
Patent Literature 2: Japanese Patent Application Laid-Open No. 2010-155187

Non Patent Literature

Non Patent Literature 1: J. A. Martens et al., J. Catal. 239 (2006), page 451

SUMMARY OF INVENTION

Technical Problem

If the isomerization selectivity of a hydroisomerization catalyst can be further increased, useful hydrocarbons, such as lubricant base oil, can be more efficiently produced.

Under these circumstances, an object of the present invention is to provide a hydroisomerization catalyst having a high isomerization selectivity and a method for producing the same; a method for dewaxing hydrocarbon oil using the hydroisomerization catalyst; a method for producing hydrocarbon; and a method for producing lubricant base oil.

Solution to Problem

The method for producing a hydroisomerization catalyst according to the present invention is characterized by including: a first step of preparing a catalyst to be treated, which contains a support having a one-dimensional porous structure including a 10-membered ring and at least one metal selected from the group consisting of: group 8 to 10 metals of the periodic table, Mo, and W supported on the hydroisomerization catalyst; and a second step of producing a hydroisomerization catalyst having a carbon content of 0.4 to 2.5% by mass by subjecting the catalyst to be treated to a coking treatment by means of a carbon-containing compound.

Hereinbelow, the carbon content of the hydroisomerization catalyst is calculated by analyzing the catalyst by an in-oxygen airflow combustion-infrared ray absorption method. More specifically, a catalyst is combusted in an oxygen airflow by means of a carbon/sulfur analysis apparatus (e.g., EMIA-920V produced by HORIBA, Ltd.) and the carbon content is determined by means of the infrared ray absorption method.

According to the method for producing a hydroisomerization catalyst according to the present invention, which includes the above-described steps, a hydroisomerization catalyst having a high isomerization selectivity can be produced.

The inventors consider that the above-described effect can be achieved due to the following reasons. The inventors consider that some of the zeolite pores are clogged by the specific coking treatment; thereby the cracking reaction is inhibited, and as a result, a catalyst with an improved isomerization selectivity is produced.

In the second step, it is preferable to produce a hydroisomerization catalyst for which the volume of micropores per unit mass of the catalyst is 0.02 to 0.11 cc/g and the volume of micropores per unit mass of the zeolite contained in the catalyst is 0.04 to 0.12 cc/g.

Hereinbelow, the volume of micropores per unit mass of the hydroisomerization catalyst is calculated by a method known as a nitrogen adsorption measurement method. More specifically, for the catalyst, the volume of micropores per unit mass thereof is calculated by analyzing an isothermal line of physical nitrogen adsorption and desorption measured at a liquid nitrogen temperature (−196° C.), i.e., by analyzing an isothermal line of nitrogen adsorption measured at a liquid nitrogen temperature (−196° C.) by a t-plot method. Furthermore, the volume of micropores per unit mass of the zeolite contained in the catalyst is calculated by the above-described nitrogen adsorption measurement method.

Hereinbelow, a "micropore" refers to a "pore having a diameter of 2 nm or less" as defined by the International Union of Pure and Applied Chemistry (IUPAC).

The present invention having the above-described steps can produce a hydroisomerization catalyst with a yet higher isomerization selectivity. The inventors consider that the above-described effect can be achieved due to the following reasons. The inventors consider that some of the zeolite pores are clogged by the specific coking treatment; thereby the cracking reaction is inhibited, and as a result, a catalyst with an improved isomerization selectivity is produced. If the volume of micropores per unit mass of the zeolite contained in the catalyst is greater than the upper limit value, the reactant is sufficiently diffused into the micropores, and the cracking reaction is considered to easily develop in the micropores, and on the other hand, if the volume of micropores per unit mass of the zeolite contained in the catalyst is less than the lower limit value, too many cokes may adhere to the inside of the zeolite micropores, which is considered to inhibit the development of the isomerization reaction.

In order to achieve a high isomerization selectivity in the hydroisomerization reaction of normal paraffins, it is preferable that the zeolite be at least one zeolite selected from the group consisting of a ZSM-22 zeolite; a ZSM-23 zeolite; an SSZ-32 zeolite; and a ZSM-48 zeolite.

The present invention is capable of providing a hydroisomerization catalyst produced by the method for producing a hydroisomerization catalyst according to the present invention.

The method for producing lubricant base oil according to the present invention is characterized in that hydrocarbon oil containing normal paraffins having 10 or more carbon atoms is contacted with the hydroisomerization catalyst according to the present embodiment in the presence of hydrogen.

According to the method for producing lubricant base oil according to the present invention, hydrocarbons suitable as lubricant base oil can be produced at a high yield by hydrotreating a hydrocarbon feedstock by means of the hydroisomerization catalyst according to the present invention under the above-described conditions.

In the method for producing lubricant base oil according to the present invention, it is preferable that the hydroisomerization catalyst be produced by subjecting a catalyst to be treated to a coking treatment at a temperature lower than a reaction temperature for hydro-isomerizing the hydrocarbon feedstock by using the hydrocarbon feedstock as a carbon-containing compound.

In the method for producing lubricant base oil according to the present invention, a hydrocarbon feedstock can be further hydrofinished and vacuum-distilled after the hydrocarbon feedstock is contacted with the hydroisomerization catalyst.

It is preferable that the hydrocarbon feedstock be at least one selected from the group consisting of: atmospheric residues; vacuum residues; a vacuum gas oil; a slack wax; and a Fischer Tropsch synthetic wax.

Advantageous Effect of Invention

According to the present invention, a hydroisomerization catalyst having a high isomerization selectivity and a method for producing the same, and a method for producing lubricant base oil using the hydroisomerization catalyst can be provided.

BRIEF DESCRIPTION OF DRAWINGS

The FIGURE is a graph illustrating a distribution of the number of carbon atoms of a feedstock wax.

DESCRIPTION OF EMBODIMENTS

<Hydroisomerization Catalyst>

Characteristics of a hydroisomerization catalyst according to the present invention are impaired thereto by producing the same by a specific method. In the following description, the hydroisomerization catalyst according to the present invention will be described with reference to preferred embodiments for producing the same.

A method for producing a hydroisomerization catalyst according to an embodiment of the present invention includes: a first step of preparing a catalyst to be treated, which contains a support having a one-dimensional porous structure including a 10-membered ring and at least one metal selected from the group consisting of: group 8 to 10 metals of the periodic table, Mo, and W supported on the hydroisomerization catalyst; and a second step of producing a hydroisomerization catalyst having a carbon content of 0.4 to 2.5% by mass by subjecting the catalyst to be treated to a coking treatment by means of a carbon-containing compound.

The carbon content of the hydroisomerization catalyst is calculated by analyzing the hydroisomerization catalyst by an in-oxygen airflow combustion-infrared ray absorption method. More specifically, a catalyst is combusted in an oxygen airflow by means of a carbon/sulfur analysis apparatus (e.g., EMIA-920V produced by HORIBA, Ltd.) and the carbon content is determined by means of the infrared ray absorption method.

In the present embodiment, in the second step, it is preferable to produce a hydroisomerization catalyst for which the volume of micropores per unit mass of the catalyst is 0.02 to 0.11 cc/g and the volume of micropores per unit mass of the zeolite contained in the catalyst is 0.04 to 0.12 cc/g.

The volume of the micropores per unit mass of the hydroisomerization catalyst is calculated by a method known as a nitrogen adsorption measurement method. More specifically, for the catalyst, the volume of micropores per unit mass thereof is calculated by analyzing an isothermal line of physical nitrogen adsorption and desorption measured at a liquid nitrogen temperature (−196° C.), i.e., by analyzing an isothermal line of nitrogen adsorption measured at a liquid nitrogen temperature (−196° C.) by a t-plot method. Furthermore, the volume of micropores per unit mass of the zeolite contained in the catalyst is calculated by the above-described nitrogen adsorption measurement method.

The volume of micropores per unit mass of the zeolite contained in the catalyst $V_Z$ can be calculated by the following expression if the binder contains no volume of micropores:

$$V_Z = V_c/M_z \times 100$$

wherein $V_c$ is a value of the volume of the micropores per unit mass of the hydroisomerization catalyst, and $M_z$ is the ratio of content (% by mass) of the zeolite contained in the catalyst.

In order to achieve a high isomerization activity and an inhibited cracking activity of normal paraffins in a hydroisomerization reaction at the same time, the zeolite contained in the catalyst to be treated according to the present embodiment has a one-dimensional porous structure including a 10-membered ring. Examples of such zeolites include AEL, EUO, FER, HEU, MEL, MFI, NES, TON, MTT, WEI,*MRE, and SSZ-32. Note that each of the above-described three-letter terms refers to a skeletal structure code defined by the Structure Commission of the International Zeolite Association (IZA) for each of classified molecular sieve-type zeolites. In addition, zeolites having the same topology are comprehensively designated by the same code.

For the zeolite, considering the high isomerization activity and the low cracking activity, zeolites having the TON structure and the MTT structure, a ZSM-48 zeolite, which is a zeolite having the *MRE structure, and an SSZ-32 zeolite are preferable among the zeolites having a one-dimensional porous structure including a 10-membered ring. For the zeolite having the TON structure, the ZSM-22 zeolite is more preferable; and for the zeolite having the MTT structure, the ZSM-23 zeolite is more preferable.

The catalyst to be treated according to the present embodiment contains at least one metal selected from the group consisting of: group 8 to 10 metals of the periodic table, Mo, and W. Examples of the group 8, group 9, and group 10 metals of the periodic table include noble metals, such as platinum, palladium, rhodium, ruthenium, iridium, and osmium, or cobalt, nickel, and iron; and platinum, palladium, nickel, and cobalt are preferable; and platinum and palladium are more preferable. It is also preferable to use the above-described metals in a combination of two or more of them, and examples of preferable combinations in this case include: a platinum/palladium combination; a cobalt/molybdenum combination; a nickel/molybdenum combination; a nickel/cobalt/molybdenum combination; a nickel/tungsten combination, and the like, and a platinum/palladium combination is more preferable. Considering the activity, the isomerization selectivity, and the persistence of the activity of the catalyst to be treated according to the present embodiment, it is preferable that the catalyst to be treated contain platinum and/or palladium.

The term "periodic table" refers to a long period periodic table of elements specified by the International Union of Pure and Applied Chemistry (IUPAC).

In the catalyst to be treated according to the present embodiment, the content of metals supported by the support containing the zeolite having a one-dimensional porous structure including a 10-membered ring is preferably 0.001 to 20% by mass, more preferably 0.01 to 5% by mass, based on the mass of the support. If the content of the supported metal is less than 0.001% by mass, it becomes difficult to impair a predetermined hydrogenation/dehydrogenation function to the catalyst. On the other hand, if the content of the metal supported is greater than 20% by mass, this content is not preferable because the phenomenon of lightening may easily develop due to the cracking of hydrocarbon on the active metal, and as a result, the yield of the fraction to be prepared tends to degrade, and moreover, the costs for the catalyst may tend to increase.

In addition, if the hydroisomerization catalyst according to the present embodiment is used for the hydroisomerization of hydrocarbon feedstock containing a large content of sulfur-containing compounds and/or nitrogen-containing compounds, considering the persistence of the catalytic activity, it is preferable that the active metal include: a nickel/cobalt combination; a nickel/molybdenum combination; a cobalt/molybdenum combination; a nickel/molybdenum/cobalt combination; a nickel/tungsten/cobalt combination, and the like. The content of the above-described metals supported in the support is preferably 0.001 to 50% by mass, and more preferably 0.01 to 30% by mass, based on the mass of the support.

It is preferable that the catalyst support to be treated contain an inorganic oxide as a binder. As the inorganic oxide, at least one inorganic oxide selected from the group consisting of: alumina; silica; titania; boria; zirconia; magnesia; ceria; a zinc oxide; a phosphorus oxide; and a complex oxide which is an oxide of a combination of two or more of the above-described oxides, is used. In order to improve the isomerization selectivity of the hydroisomerization catalyst, silica and alumina are preferable among them, and alumina is more preferable. In addition, the "complex oxide which is an oxide of a combination of two or more of the above-described oxides" is a complex oxide including at least two of alumina, silica, titania, boria, zirconia, magnesia, ceria, a zinc oxide, and a phosphorus oxide, and a complex oxide having alumina containing alumina component of 50% by mass based on the complex oxide as the main component thereof is preferable; and alumina-silica is particularly more preferable.

For the catalyst support to be treated, it is preferable that the combination ratio between the zeolite having a one-dimensional porous structure including a 10-membered ring and the inorganic oxide be 10:90 to 90:10, and more preferably be 30:70 to 85:15, as the ratio of the zeolite to the inorganic oxide. If this ratio is less than 10:90, the ratio is not preferable because the activity of the hydroisomerization catalyst tends to become insufficiently high in this case. On the other hand, if this ratio is higher than 90:10, the ratio is not preferable because the mechanical strength of the support prepared by extruding and calcining the composition tends to become insufficiently high in this case.

The method for combining the inorganic oxide with the zeolite having a one-dimensional porous structure including a 10-membered ring is not limited to a specific method, and a usual method can be employed, in which a viscous fluid is prepared by adding liquid, such as a proper amount of water, to the powder of the zeolite having a one-dimensional porous structure including a 10-membered ring and the inorganic oxide, and the resulting viscous fluid is kneaded by means of a kneading machine and the like.

The composition containing the zeolite having a one-dimensional porous structure including a 10-membered ring and the inorganic oxide or the viscous fluid containing the composition is extruded by a method such as extrusion extruding, and is then preferably be dried, to be reduced to particulate extruded body. The shape of the extruded body is not particularly limited, and examples of the shape of the extruded body include a cylindrical shape, a pellet-like shape, a spherical shape, a deformed cylindrical shape having a trefoil or quatrefoil cross section, and the like. The dimension of the extruded body is not particularly limited, and considering the ease of handling the extruded body and the packing density of the extruded body in the reactor, it is preferable that the extruded body have a major axis of about 1 to 30 mm and a minor axis of about 1 to 20 mm.

The method for carrying the metal on the catalyst support to be treated is not limited to a specific method, and a known method usually applied in producing a hydroisomerization catalyst can be used. In usual cases, it is preferable to use a method in which a solution containing a salt of an active metal is impregnated into the catalyst support. In addition, an equilibrium adsorption method, a pore-filling method, an incipient-wetness method are preferably employed. For example, the pore-filling method is a method in which a volume of micropores included in a support is previously measured and a metal salt solution having the same volume as that of the micropores is impregnated, and in this method, the impregnation method is not limited to a specific method, and the impregnation can be carried out by an appropriate method according to the content of metals supported and the physical properties of the catalyst support.

It is preferable that the catalyst to be treated according to the present invention be a catalyst that has undergone reduction preferably after being charged to a reactor in which coking treatment is carried out. More specifically, it is preferable that the catalyst to be treated according to the present invention be a catalyst that has undergone reduction for 0.5 to 5 hours in an atmosphere containing molecular hydrogen, preferably under a hydrogen gas flow, preferably at 250 to 500° C., more preferably at 300 to 400° C. By carrying out the above-described steps, a high activity on the dewaxing of the hydrocarbon feedstock can be more securely impaired to the catalyst.

Examples of the carbon-containing compound used in the coking treatment include: a light organic solvent containing no oxygen or sulfur component; and hydrocarbon oil containing normal paraffins having 10 or more carbon atoms. For the hydrocarbon oil, hydrocarbon oil containing normal paraffins having 15 or more carbon atoms is preferable. More specifically, examples of the hydrocarbon oil include: relatively light distilled fractions, such as kerosene and jet fuels; and high boiling point feedstocks, such as: fuel fractions or wax fractions deriving from any type of crude oils, atmospheric distillation residues, vacuum tower residues, vacuum residues, cycle stocks, syncrudes (e.g., shale oil, tar oil, and the like), gas oil, vacuum gas oil, foot's oil, and FT synthetic oil; and other heavy oils.

If the solvent is extremely rich in oxygen or sulfur components, such solvent is not preferable because the active metals may be poisoned during the coking treatment, which may shorten the life of the catalyst.

In the present embodiment, a dewaxing raw material is preferable as the carbon-containing compound, which undergoes a dewaxing treatment by means of a hydroisomerization catalyst. In other words, a hydroisomerization catalyst with an improved isomerization selectivity can be produced by coking the catalyst to be treated charged in a reactor by means of the dewaxing raw material, and a treatment for dewaxing the dewaxing raw material can be carried out subsequently to the coking treatment. It is preferable to use such dewaxing raw material as the carbon-containing compound because it is not necessary to newly substitute the atmosphere of the system in this case, which may reduce operation costs. Examples of the dewaxing raw material include a hydrocarbon feedstock used in the following lubricant base oil production method.

However, if the dewaxing raw material includes an excessively large content of a heavy raw material, a drift may occur in the reactor; as a result, cokes may be partially easily generated, and therefore a light dewaxing raw material is preferable.

For a coking temperature, a temperature of 300 to 350° C. is preferable, a temperature of 310 to 325° C. is more preferable, and a temperature of 310 to 315° C. is yet more preferable. If the coking temperature is higher than 350° C., aromatic hydrocarbons are generated; in this case, excessive coking may easily occur, and as a result, it becomes difficult to control the clogging of the pores of the zeolite. If the coking temperature is lower than 300° C., coking may hardly occur, and in this case, it tends to become difficult to achieve the effect of the present invention.

For a liquid hourly space velocity (LHSV) of the dewaxing raw material for the coking treatment, an LHSV of 0.05 to 0.8 $h^{-1}$ is preferable, an LHSV of 0.1 to 0.8 $h^{-1}$ is more preferable, and an LHSV of 0.1 to 0.5 $h^{-1}$ is yet more preferable. If the LHSV is lower than 0.05 $h^{-1}$, the accuracy of measurement hardware may degrade; in this case, it tends to become difficult to stably supply the raw material, and if the LHSV is higher than 0.8 $h^{-1}$, the cracking activity may tend to degrade.

In the present embodiment, it is preferable that the coking temperature be lower than the temperature set in the dewaxing treatment and that the liquid hourly space velocity for the dewaxing raw material set for the coking treatment be lower than the liquid hourly space velocity for the dewaxing raw material set for the dewaxing treatment.

For the pressure for the coking treatment, a pressure of 0.1 to 20 MPa is preferable, and a pressure of 0.5 to 15 MPa is more preferable.

In addition, in the present embodiment, the coking treatment is carried out so that the carbon content of the catalyst becomes 0.4 to 2.5% by mass, preferably 0.4 to 2.0% by mass. In addition, it is preferable that the coking treatment be carried out so that the volume of micropores per unit mass of the catalyst becomes 0.02 to 0.11 cc/g and that the volume of micropores per unit mass of the zeolite contained in the catalyst becomes 0.04 to 0.12 cc/g. Accordingly, the present invention can achieve high levels of activity and isomerization selectivity of the hydroisomerization catalyst at the same time.

The inventors consider that the above-described effect can be achieved due to the following reasons. Isomerization active sites for the hydroisomerization catalyst according to the present embodiment are considered to exist in the vicinity of a micropore mouth. In order to promote the isomerization reaction, it is necessary to improve a contact efficiency between the isomerization active site and the reactant; and in order to achieve this, zeolites having a one-dimensional porous structure including a 10-membered ring with pores large enough to allow the reactant to be diffused into the pores are used. On the other hand, cracking active sites exist uniformly on an external surface of the catalyst and inside the pores, and if the pores are excessively large, the reactant may be sufficiently diffused in the pores; in this case, the cracking reaction can be easily promoted. The inventors consider that in the coking treatment according to the present embodiment, the diffusion of the reactant is inhibited due to the cokes adhered inside the pores in a small content, and thus the cracking is inhibited. However, the inventors consider that it is also important not to allow an excessive content of cokes to adhere to the inside of the pores because the isomerization active sites exist in the vicinity of micropore mouths. If a great content of cokes are allowed to adhere to the inside of the pores, the reactants cannot be diffused into the pores because the pores are clogged, the isomerization reaction may not appropriately develop because the active sites are covered, and as a result, the degree of conversion of normal paraffins may tend to become insufficiently high.

<Method for Producing Lubricant Base Oil>

Now, the lubricant base oil production method according to the present invention will be described below. The lubricant base oil production method according to the present embodiment includes a step for contacting a hydrocarbon feedstock, which contains normal paraffin having 10 or more carbon atoms, with the hydroisomerization catalyst according to the present invention described above, in the presence of hydrogen.

The hydrocarbon feedstock (dewaxing raw material) is not limited to a specific type if the hydrocarbon feedstock contains normal paraffin having 10 or more carbon atoms, and it is preferable that the hydrocarbon feedstock contain normal paraffin having 15 or more carbon atoms. More specifically, examples of the hydrocarbon feedstock include various types of oil, such as: relatively light distilled fractions, such as kerosene and jet fuels; and high boiling point feedstocks, such as: fuel fractions or wax fractions deriving from any type of crude oil, atmospheric distillation residues, vacuum tower residues, vacuum residues, cycle stocks, syncrudes (e.g., shale oil, tar oil, and the like), gas oil, vacuum gas oil, foot's oil, and FT synthetic oil; and other heavy oil. In addition, the above-described hydrocarbon feedstock may contain wax components including naphthenic hydrocarbons having a long, straight chain alkyl group or a wax component including aromatic hydrocarbons as a side chain in addition to the normal paraffin.

For the hydrocarbon feedstock used in the present embodiment, hydrocarbon oil including hydrocarbons having 10 or more carbon atoms having a boiling point of about 180° C. or higher is particularly preferable. Hydrocarbon oil lighter than the above-described hydrocarbon feedstock usually contain substantially no wax components that influence the fluidity in low-temperature conditions, and therefore, it becomes difficult to achieve the effect of the present invention because the necessity to carry out dewaxing is low in this case.

On the other hand, it is especially effective to apply the dewaxing by means of the hydroisomerization catalyst according to the present invention to: distillate feedstocks containing wax components, i.e., middle distillate feedstocks including gas oils, kerosenes, and jet fuels; lubricant feedstocks; and heating oils, and in addition, other distilled fractions for which pour points and the viscosity are required to be kept within a predetermined range. Examples of such hydrocarbon oil include hydrotreated or hydrocracked oil, such as: a gas oil, a heavy gas oil, a vacuum gas oil, atmospheric residues, vacuum residues, lube raffinate, a lubricant raw material, a bright stock, a slack wax (rough wax), a foot's oil, a deoiling wax, a paraffin wax, a microcrystalline wax, petrolatum, a synthetic oil, an FT synthetic oil, high pour point polyolefines, a straight chain α-olefin wax, and the like. These can be used singly or in combinations of two or more. In particular, it is preferable that the hydrocarbon oil be at least one selected from the group consisting of: vacuum gas oil, hydrocracked vacuum gas oil, atmospheric residues, hydrocracked atmospheric residues, vacuum residues, hydrocracked vacuum residues, a slack wax, a dewaxed oil, a paraffin wax, a microcrystalline wax, petrolatum, and a Fischer Tropsch synthetic wax, and more preferably be at least one selected from the group consisting of: atmospheric residues, vacuum residues, a vacuum gas oil, a slack wax, and a Fischer Tropsch synthetic wax.

A preferable hydroisomerization temperature is 200 to 450° C., and a temperature of 220 to 400° C. is more preferable. If the reaction temperature is lower than 200° C., the isomerization of normal paraffins contained in the hydrocarbon feedstock, which is a raw material, may not appropriately develop, and as a result, the wax components may tend to be insufficiently reduced or eliminated. On the other hand, if the reaction temperature is higher than 450° C., the cracking of hydrocarbon feedstock becomes remarkable and the yield of the hydrocarbon suitable for the lubricant base oil to be produced tends to degrade.

For the pressure for hydroisomerization reaction, a pressure of 0.1 to 20 MPa is preferable, and a pressure of 0.5 to 15 MPa is more preferable. If the reaction pressure is below 0.1 MPa, the degradation of the catalyst may be accelerated due to cokes generated during the reaction. On the other hand, if the reaction pressure is higher than 20 MPa, an economical process may tend to be difficult to achieve because the apparatus construction costs may increase.

A liquid space velocity of the hydrocarbon tock to the catalyst is preferably 0.01 to 100 $h^{-1}$, and more preferably 0.1 to 50 $h^{-1}$. If the liquid space velocity is lower than 0.01 $h^{-1}$, the cracking of the hydrocarbon feedstock may excessively easily develop, and thus the production efficiency for the hydrocarbon suitable for the lubricant base oil to be produced may tend to decrease. On the other hand, if the liquid hourly space velocity is higher than 100 $h^{-1}$, the development of the isomerization of normal paraffins contained in hydrocarbon feedstock may be inhibited, and as a result, the reduction and elimination of wax components may tend to become insufficient.

A feed ratio of hydrogen and hydrocarbon feedstock is preferably 100 to 1,000 $Nm^3/m^3$, and more preferably 200 to 800 $Nm^3/m^3$. If the feed ratio is below 100 $Nm^3/m^3$ and if the feedstock contains sulfur compounds and nitrogen compounds, the predetermined catalytic performance may tend to become difficult to achieve because hydrogen sulfides and ammonium gas generated by desulfurization and denitrogenation reactions occurring concurrently with the isomerization reaction may be poisoned by adsorbing active metals on the catalyst. On the other hand, if the feed ratio is higher than 1000 $Nm^3/m^3$, an economical process may tend to become difficult to achieve because a large-capacity hydrogen feeding facilities become necessary.

The degree of conversion of the normal paraffin in the hydroisomerization reaction is appropriately adjusted according to the purpose of use of the lubricant base oil to be produced. In the present embodiment, it is preferable that a hydrocarbon feedstock containing normal paraffins having 10 or more carbon atoms be contacted with the hydroisomerization catalyst according to the present invention under conditions by which the degree of conversion of normal paraffins defined by the following expression (I) becomes substantially 100% by mass:

Normal paraffin conversion (%)=[1−(Total amount of normal paraffins equal to or greater than $Cn$ contained in contacted hydrocarbon feedstock)/ (Total amount of normal paraffins equal to or greater than $Cn$ contained in hydrocarbon feedstock yet to be contacted)×100   (I)

wherein Cn is the lowest number of carbon atoms for normal paraffins having 10 or more carbon atoms contained in the hydrocarbon feedstock yet to be contacted.

In the present embodiment, the description such that "the degree of conversion . . . becomes substantially 100% by mass" refers to a condition such that the content of the normal paraffins contained in the contacted hydrocarbon feedstock is 0.1% by mass or lower.

The hydrocarbon feedstock used in the lubricant base oil production method according to the present invention is not limited to a specific type if the hydrocarbon feedstock contains normal paraffin having 10 or more carbon atoms, and it is preferable that the hydrocarbon feedstock contain hydrocarbon oil with an initial boiling point higher than that of lubricant base oil to be produced. As the above-described feedstock, fractions having a boiling point in terms of atmospheric pressure of higher than 360° C., such as petroleum fractions, synthetic oil, and synthetic wax are suitable; more specifically, examples of such feedstocks include: atmospheric residues; heavy gas oil; vacuum residues; a vacuum gas oil; lube raffinate; a bright stock; a slack wax (rough wax); foot's oil; a deoiling wax; a paraffin wax; a microcrystalline wax; petrolatum; a synthetic oil; an FT synthetic oil; an FT synthetic wax; high pour point polyolefins; a straight chain α-olefin wax, and the like. It is particularly preferable to use atmospheric residues, a vacuum gas oil, vacuum residues, a slack wax, an FT synthetic oil, and an FT synthetic wax. These can be used singly or in combinations of two or more. In addition, it is preferable that the above-described oil be previously treated by hydrotreating or mild hydrocracking. By carrying out the above-described treatment, sulfur-containing compounds, materials that may degrade the activity of hydroisomerization catalysts such as nitrogen-containing compounds, and materials that may degrade the viscosity index of lubricant base oil, such as aromatic hydrocarbon, naphthenic hydrocarbon, and the like, can be decreased or eliminated.

The isomerization of the normal paraffins contained in the hydrocarbon oil, i.e., the dewaxing reaction of the hydrocarbon oil, can be allowed to develop while sufficiently inhibiting the phenomenon of lightening by contacting the relatively heavy hydrocarbon oil, which is a feedstock, with the hydroisomerization catalyst according to the present invention in the presence of hydrogen. Thus, hydrocarbon with a ratio of 90% by volume or higher of fractions having a boiling point in tennis of atmospheric pressure is higher than 360° C. can be produced at a high yield. In addition, according to the lubricant base oil production method of the present invention, base oil containing a large content of isomers having a branched chain structure can be produced. In particular, it is required for high quality lubricant base oil to contain 0.1% by mass or less normal paraffin, and according to the method for producing lubricant base oil of the present invention, lubricant base oil that satisfies the quality requirement can be produced at a high yield.

In the hydroisomerization of hydrocarbon feedstock containing normal paraffins, the degree of conversion of normal paraffins can be usually increased by raising the reaction temperature, for example, and thus the content of normal paraffins in the reaction product to be produced can be lowered, and accordingly, the fluidity of hydrocarbon oil in low temperature conditions can be improved. However, if the reaction temperature is raised, the cracking reaction of the hydrocarbon oil, which is a feedstock, and an isomerization product may be promoted, and accordingly, light fractions may increase as the conversion of normal paraffins rises. The increase in the light fractions may cause the decrease of the viscosity index of hydrocarbon oil, and therefore, in order to set the performance of the lubricant base oil within a predetermined range, it is necessary to separate and eliminate the light fractions by distillation or the like. In particular, in producing the following high-performance lubricant base oil including Group II, III, and III+ oils, or the like classified as lubricant grade oils by the American Petroleum Institute (API) (specified requirements for these oils are as follows) by catalytic dewaxing of the above-described hydrocarbon feedstocks, it is required that the conversion of the normal paraffins contained in the hydrocarbon oil, which is the raw material, is substantially 100%:

Group II oils: viscosity index of 80 or greater and below 120; saturates of 90% by mass or greater; and sulfur content of 0.03% by mass or lower)

Group III oils: viscosity index of 120 or greater; saturates of 90% by mass or greater; and sulfur content of 0.03% by mass or lower)

Group III+ oils: viscosity index of 140 or greater; saturates of 90% by mass or greater; and sulfur content of 0.03% by mass or lower). In conventional methods for producing lubricant base oil using a catalyst for catalytic dewaxing, if a condition for achieving the 100% conversion of normal paraffins is employed, the yield of the above-described high-performance lubricant base oils may become extremely low. According to the lubricant base oil production method of the present invention, even if the condition for achieving the 100% conversion of normal paraffins is employed in carrying out the hydrotreating step, the yield for the above-described high-performance lubricant base oils can be maintained at a high level.

Facilities for implementing the lubricant base oil production method according to the present embodiment are not limited to specific types and known facilities can be used. For reaction facilities, any of continuous flow type, batch type, and semi-batch type facilities can be used, and the continuous flow type is preferable considering the productivity and the efficiency. For a catalyst layer, any of an immobilized bed, a fluidized bed, and an agitating bed can be used, and the immobilized bed is preferable considering the facility costs and the like. A reactional phase is preferably a gas-liquid mixed phase.

In the lubricant base oil production method according to the present embodiment, it is preferable to produce a hydroisomerization catalyst by carrying out the coking treatment with the dewaxing raw material before a dewaxing step carried out by the hydroisomerization reaction.

In addition, in the lubricant base oil production method according to the present embodiment, the hydrocarbon oil, which is the raw material to be fed, can be hydrotreated or hydrocracked at a stage prior to the dewaxing step carried out by the hydroisomerization reaction. In this case, known facilities, catalyst, and reaction conditions are used. By executing the above-described pretreatments, the activity of the hydroisomerization catalyst according to the present invention can be maintained for a long period, and in addition, environmental burden-substances contained in the products, such as sulfur-containing compounds and nitrogen-containing compounds, can be reduced.

In the method for producing lubricant base oil according to the present embodiment, the reaction product produced after undergoing the catalytic dewaxing, in which the hydrocarbon feedstock is contacted with the hydroisomerization catalyst according to the present invention, can be further treated by hydrofinishing, for example. The hydrofinishing can be implemented generally by contacting a product to be finished with a metal carrying hydrogenation catalyst (e.g., platinum supported by alumina) in the presence of hydrogen. By performing the hydrofinishing described above, the hue, the oxidation stability, and the like of the reaction product produced by the dewaxing step can be improved, and as a result, the product quality can be improved. The hydrofinishing can be implemented by reaction facilities provided separately from those for the dewaxing step; alternatively, the hydrofinishing can be carried out just after the dewaxing step in a catalyst layer for hydrofinishing, which can be provided on a downstream side of a catalyst layer for the hydroisomerization catalyst according to the present embodiment, which is provided within the reactor for the dewaxing step.

Note that the term "isomerization" usually refers to a reaction in which the molecular structure only changes without any change in the number of carbon atoms (molecular mass) and the term "cracking" refers to a reaction in which the number of carbon atoms (molecular mass) decreases. In the isomerization dewaxing reaction which utilizes the isomerization reaction, if cracking of the raw material hydrocarbon oil and products of the isomerization occurs to a degree, such degree of cracking may not become intolerable if the number of carbon atoms (molecular mass) of the product comes within a predetermined range in which the base oil to be produced can be constituted, and a cracking product can be a component of the base oil.

The method for producing lubricant base oil is described above, and according to the hydroisomerization catalyst of the present invention, hydrocarbon oils suitable for fuel base oils can also be produced because hydrocarbon feedstocks can be dewaxed in a similar manner as described above, by contacting a hydrocarbon feedstock containing normal paraffins having 10 or more carbon atoms with the hydroisomerization catalyst according to the present invention.

EXAMPLES

[Production of Hydroisomerization Catalyst]

Production Example 1

<Production of ZSM-22 Zeolite>

A ZSM-22 zeolite (hereinafter simply referred to as "ZSM-22") including a crystalline aluminosilicate having the Si/Al ratio of 45 was produced by hydrothermal synthesis in the following manner.

At the start of the operation, the following four types of aqueous solutions were prepared.

Solution A: a solution prepared by dissolving 1.94 g of potassium hydroxide in 6.75 mL of deionized water.

Solution B: a solution prepared by dissolving 1.33 g of aluminum sulfate octadecahydrate in 5 mL of deionized water.

Solution C: a solution prepared by diluting 4.18 g of 1,6-hexanediamine (organic template) in 32.5 mL of deionized water.

Solution D: a solution prepared by diluting 18 g of colloidal silica (Ludox AS-40 manufactured by Grace Davison) in 31 mL of deionized water.

Then, the solution A was added to the solution B, and the mixture was agitated until aluminum components were completely dissolved. The solution C was added to the mixed solution, then the mixed solution containing the solutions A, B, and C was intensely agitated at room temperature and the agitated mixed solution was poured into the solution D. 0.25 g of powder of ZSM-22, which had been separately synthesized as a "seed crystal" for accelerating crystallization and which had not undergone any special treatment after the synthesis, was added to the mixed solution to obtain a gelled substance.

The gelled substance prepared by the above-described operation was transferred into a stainless steel autoclave reactor having an internal volume of 120 mL, the autoclave reactor was rotated on a tumbling apparatus for 60 hours in an oven kept at 150° C. at the rotation speed of about 60 rpm to run a hydrothermal synthesis reaction. After the reaction was completely run, the reactor was cooled down, opened, and dried overnight in a drier kept at 60° C., and as a result, a ZSM-22 having the Si/Al ratio of 45 was produced.

<Ion Exchange of ZSM-22 Including Organic Templates>

An ion-exchanging treatment was carried out for the ZSM-22 produced in the above-described manner in an aqueous solution containing ammonium ions by the following operations.

The ZSM-22 produced in the above-described manner was transferred into a flask, then 100 mL of 0.5 N-ammonium chloride aqueous solution for 1 g of ZSM-22 zeolite was added, and the mixture was heated under reflux for 6 hours. Then the mixture was cooled down to room temperature, the supernatant liquid was removed, and the crystalline aluminosilicate was washed in the deionized water. The same amount of a 0.5 N-ammonium chloride aqueous solution as that described above was added to the mixture again, and the mixture was heated under reflux for 12 hours.

Subsequently, solid contents were extracted by filtration, the extracted solid contents were then washed with the deionized water, dried overnight in a drier kept at 60° C., and thus an ion-exchanged $NH_4$-ZSM-22 was produced. The ZSM-22 was ion-exchanged in a state in which organic templates were contained.

<Mixing of Binder, Extruding, Calcination>

The $NH_4$-ZSM-22 produced by the above-described operation and alumina, which was used as a binder, were mixed at the mass ratio of 7:3, then a small amount of deionized water was added to the mixture, and then the mixture was kneaded. The produced viscous fluid was charged into an extruder to be extruded, and a cylindrical extruded body having the diameter of about 1.6 mm and the length of about 10 mm was prepared. This extruded body was heated for 3 hours at 400° C. under an air atmosphere, and a support precursor was produced.

<Carrying of Platinum, Calcination>

A tetraammineplatinum dinitrate $[Pt(NH_3)_4](NO_3)_2$ was dissolved in deionized water equivalent to a previously measured water absorption of the support precursor, and an impregnation solution was prepared. The solution was impregnated into the support precursor by an incipient wetness method, and carrying was performed so as to allow 0.3% by mass of platinum to be supported on the ZSM-22 based on the mass of the ZSM-22 zeolite. The produced impregnated substance (catalyst precursor) was dried overnight in the drier kept at 60° C., then the dried substance was calcined at 400° C. for 3 hours under an air flow, and a hydroisomerization catalyst E-1 was produced.

Production Example 2

<Production of ZSM-48 Zeolite>

A ZSM-48 zeolite with the Si/Al ratio of 45 containing organic templates (hereinafter may be simply referred to as "ZSM-48") was synthesized on the basis of "Applied Catalysis A: General", vol. 299(2006):167-174.

The following four types of reagents were prepared.
Reagent E: 2.97 g of sodium hydroxide
Reagent F: 0.80 g of aluminum sulfate octadecahydrate
Reagent G: 26.2 g of 1,6-hexanediamine (organic template)
Reagent H: 0.9 mL of 98% sulfuric acid solution
Reagent I: 75 g of aqueous solution ($SiO_2$ concentration: 40%) of colloidal silica (Ludox AS-40 manufactured by Grace Davison)

The reagents E through I were then added to 180 mg deionized water and the mixture was agitated for 2 hours at room temperature until the reagents were completely dissolved therein.

The gelled substance prepared by the above-described operation was transferred into a stainless steel autoclave reactor having an internal volume of 100 mL, the autoclave reactor was rotated on a tumbling apparatus for 60 hours in an oven kept at 160° C. at the rotation speed of about 60 rpm to run a hydrothermal synthesis reaction. After the reaction was completely run, the reactor was cooled down, opened, and dried overnight in a drier kept at 60° C., and a ZSM-22 having the Si/Al ratio of 45 was produced.

<Ion Exchange of ZSM-48 Including Organic Templates>

An ion-exchanged $NH_4$-ZSM-48 was prepared by carrying out an operation similar to that performed in the ion exchange of ZSM-22 in the example 1 except that a ZSM-48 including organic templates prepared in the above-described manner was used instead of the ZSM-22 including organic templates.

A hydroisomerization catalyst E-2 was produced by producing an extruded body, heating the extruded body, preparing a catalyst precursor, and calcining the catalyst precursor by an operation similar to that in the production example 1 except that the $NH_4$-ZSM-48 prepared in the above-described manner was used instead of the $NH_4$-ZSM-22.

Production Example 3

<Production of SSZ-32 Zeolite>

An SSZ-32 zeolite (hereinafter may also be simply referred to as an "SSZ-32") was produced by hydrothermal synthesis in conformity with the method described in JP 2006-523136 A in the following manner.

Sodium hydroxides, aluminum sulfates, colloidal silica, isobutylamines, and N-methyl-N'-isopropyl-imidazolium cations were prepared by mixing at the following molar ratios:

$SiO_2/Al_2O_3$=35, and the total content of the isobutylamine and the N-methyl-N'-isopropyl-imidazolium cation was 0.2 times as large as the content of $SiO_2$.

The gelled substance prepared by the above-described operation was transferred into a stainless steel autoclave reactor having an internal volume of 100 mL, the autoclave reactor was rotated on a tumbling apparatus for 60 hours in an oven kept at 160° C. at the rotation speed of about 60 rpm to run a hydrothermal synthesis reaction. After the reaction was completely run, the reactor was cooled down, opened, and dried overnight in a drier kept at 60° C., and an SSZ-32 having the Si/Al ratio of 45 was produced.

<Ion Exchange of SSZ-32 Including Organic Templates>

An ion-exchanged $NH_4$-SSZ-32 was prepared by carrying out an operation similar to that performed in the ion exchange of ZSM-22 in the production example 1 except that an SSZ-32 including organic templates and prepared in the above-described manner was used instead of the ZSM-22 including organic templates.

A hydroisomerization catalyst E-3 was produced by producing an extruded body, heating the extruded body, preparing a catalyst precursor, and calcining the catalyst precursor by an operation similar to that in the production example 1 except that the $NH_4$-SSZ-32 prepared in the above-described manner was used instead of the $NH_4$-ZSM-22.

Production Example 4

A hydroisomerization catalyst E-4 was produced in a similar manner as the production example 1 except that the calcining conditions for producing the support precursor were changed from those of the production example 1, i.e., the support precursor was heated at 300° C. for 3 hours under an $N_2$ atmosphere.

Production Example 5

The steps of the production example 1 up to the step for producing the ZSM-22 were performed in the similar manner, then the produced ZSM-22 and alumina, i.e., a binder, were mixed at a mass ratio of 7:3, then a small content of deionized water was added to the mixture, and the mixture was kneaded. The produced viscous fluid was charged into an extruder to be extruded, and a cylindrical extruded body having the diameter of about 1.6 mm and the length of about 10 mm was prepared. This extruded body was heated for 3 hours at 400° C. under an air atmosphere, and an extruded body ZSM-22 was produced.

An ion-exchanging treatment was carried out for the extruded body ZSM-22 with an aqueous solution containing ammonium ions by the following operations.

The ZSM-22 produced in the above-described manner was transferred into a flask, then 100 mL of 0.5 N-ammonium chloride aqueous solution for 1 g of ZSM-22 zeolite was added, and the mixture was heated under reflux for 6 hours. Then the mixture was cooled down to room temperature, the supernatant liquid was removed, and the crystalline aluminosilicate was washed in the deionized water. The same amount of a 0.5 N-ammonium chloride aqueous solution as that described above was added to the mixture again, and the mixture was heated under reflux for 12 hours.

Subsequently, solid contents were extracted by filtration, the extracted solid contents were then washed with the deionized water, dried overnight in a drier to produce an ion-exchanged $NH_4$-ZSM-22. The ZSM-22 was ion-exchanged in a state in which organic templates were contained.

A tetraammineplatinum dinitrate $[Pt(NH_3)_4](NO_3)_2$ was dissolved in deionized water equivalent to a previously measured water absorption of the support precursor to prepare an impregnation solution. The solution was impregnated into the support precursor by an incipient wetness method, and carrying was performed so as to allow 0.3% by mass of platinum to be supported on the ZSM-22 based on the mass of the ZSM-22 zeolite. The produced impregnated substance (catalyst precursor) was dried overnight in the drier kept at 60° C., then the dried substance was calcined for 3 hours at 400° C. under an air flow, and a hydroisomerization catalyst E-5 was produced.

Production Example 6

A hydroisomerization catalyst E-6 was produced in a similar manner as the production example 1 except that the calcining conditions for producing the support precursor were changed from those of the production example 1, i.e., the support precursor was heated at 300° C. for 3 hours under an $N_2$ atmosphere and that the calcining conditions for producing the catalyst precursor were changed from those of the production example 1, i.e., the catalyst precursor was heated at 350° C. for 3 hours under an air atmosphere.

<Production of Lubricant Base Oil>

By using each of the catalysts produced in the above-described manner, a wax was dewaxed and lubricant base oil fractions were separated and collected.

Example 1

A wax was dewaxed with the hydroisomerization catalyst E-1. Before the dewaxing treatment, the following coking treatment was performed.

[Coking Treatment]

100 mL of the extruded catalyst was charged into a stainless steel reaction tube having an inner diameter of 15 mm and a length of 380 mm, and a reduction treatment was carried out at a catalyst layer average temperature of 350° C. for 12 hours under a hydrogen flow (hydrogen partial pressure: 3 MPa). Then, a petroleum slack wax (a neutral slack wax 150 having a distribution of the number of carbon atoms C10 to C40: the composition of this slack wax is illustrated in the FIGURE) was run, as a raw material, at a reaction temperature of 320° C., a hydrogen partial pressure of 3 MPa, an LHSV of 0.5 $h^{-1}$, and a hydrogen/oil ratio of 500 NL/L, a coking treatment was started, and the treatment was terminated after 100 hours from its start. Note that in the FIGURE, the letter "A" denotes the content of non-normal paraffins and the letter "B" denotes the content of normal paraffins.

[Properties of Catalyst Before and after the Coking Treatment]

The carbon content of the catalyst after the coking treatment and the volume of micropores per unit mass of the zeolite contained in the catalyst before and after the coking treatment was performed thereto were measured by the following method.

The carbon content of the catalyst after the coking treatment was performed thereto was measured by an in-oxygen airflow combustion-infrared ray absorption method. More specifically, the catalyst was calcined in an oxygen airflow and the carbon content was determined by means of infrared ray absorption method using EMIA-920V manufactured by HORIBA, Ltd. as a measuring device.

For the measurement of the volume of micropores, in order to eliminate water contents adsorbed by the catalyst first, an evacuation pretreatment was carried out for 5 hours at 150° C. For the pretreated catalyst, nitrogen adsorption measurement was carried out by means of BELSORP-max manufactured by BEL JAPAN, INC. at a liquid nitrogen temperature (−196° C.). The measured isothermal line of nitrogen adsorption was analyzed by a t-plot method, and the volume of micropores per unit mass of the catalyst (cc/g) was calculated before and after the coking treatment.

Furthermore, the volume $V_Z$ of micropores per unit mass of the zeolite contained in the catalyst was calculated according to the following expression. Note that by carrying out the nitrogen adsorption measurement in the similar manner as that described above on alumina, which was used as the binder, it was observed that alumina included no micropores.

$$V_Z = V_c/M_z \times 100$$

wherein $V_c$ is a value of the volume of the micropores per unit mass of the hydroisomerization catalyst, and $M_z$ is the ratio of content (% by mass) of the zeolite contained in the catalyst.

[Pilot Study for Calculating Tc]

The following pilot study was performed prior to the isomerization dewaxing treatment by using the same catalyst (E-1) to calculate the reaction temperature Tc (° C.) for the isomerization dewaxing treatment. 100 mL of the extruded catalyst was charged into a stainless steel reaction tube having an inner diameter of 15 mm and a length of 380 mm, and a reduction treatment was carried out at a catalyst layer average temperature of 350° C. for 12 hours under a hydrogen flow (hydrogen partial pressure: 3 MPa). Then, the above-described raw material was run at a reaction temperature of 310 to 330° C., a hydrogen partial pressure of 3 MPa, an LHSV of 1.0 h$^{-1}$, and a hydrogen/oil ratio of 500 NL/L, and a dewaxing treatment by a hydroisomerization dewaxing reaction was started. The reaction was run for 72 hours and the reaction product was collected and analyzed.

Subsequently, the reaction temperature was raised in stages up to about 350° C. to increase the feedstock conversion with the hydrogen partial pressure, the LHSV, and the hydrogen/oil ratio unchanged. The reaction was run for 72 hours at respective reaction temperatures and when the reaction became stable, each reaction product was sampled and analyzed.

On the basis of results of the analysis on each of the reaction products, each reaction product produced at a reaction temperature at which the conversion of normal paraffins was 100%, which is defined by the above-described expression (I), fractionation was performed by the following operations and the following lubricant base oil fractions were separated and collected.

The reaction products produced at each reaction temperature at which the conversion of the normal paraffins was 100% were at first fractionated into a naphtha fraction, a kerosene and gas oil fraction, and heavy fraction. Furthermore, the heavy fraction was fractionated into a lubricant base oil fraction with a boiling point ranging from 330 to 410° C. and a kinetic viscosity of 2.7±0.1 cSt at 100° C. (this fraction will be hereinafter referred to as a "lubricant base oil fraction 1"), and a lubricant base oil fraction with a boiling point ranging from 410 to 450° C. and a kinetic viscosity of 4.0±0.1 cSt at 100° C. (this fraction will be hereinafter referred to as a "lubricant base oil fraction 2"). A lowest reaction initial temperature, at which the pour point of the lubricant base oil fraction 2 becomes −22.5° C. or lower and the viscosity index becomes 140 or greater, was taken as a reaction initial temperature Tc (° C.).

[Dewaxing of Wax]

After the coking treatment, the wax was run under the conditions reached by the above-described method, in which the reaction temperature Tc=325° C. and the LHSV=1.0 h$^{-1}$, with the hydrogen partial pressure and the hydrogen/oil ratio being maintained, and a dewaxing treatment by the hydroisomerization reaction was started.

[Separation/Collection of Lubricant Base Oil Fraction]

Reaction products were collected at timings of 10 hours and 100 hours after the reaction started and the yields for the lubricant base oil fractions 1 and 2 were calculated.

Example 2

The yields of the lubricant base oil fractions 1 and 2 were calculated in the similar manner as the example 1 except that the coking treatment was performed on the catalyst E-1 at the reaction temperature of 350° C. and the LHSV of 0.5 h$^{-1}$.

Example 3

The yields of the lubricant base oil fractions 1 and 2 were calculated in the similar manner as the example 1 except that the coking treatment was performed on the catalyst E-1 at the reaction temperature of 320° C. and the LHSV of 0.1 h$^{-1}$.

Example 4

The yields of the lubricant base oil fractions 1 and 2 were calculated in the similar manner as the example 1 by performing the coking treatment and the dewaxing treatment except that the catalyst E-4 was used instead of the catalyst E-1.

Example 5

The yields of the lubricant base oil fractions 1 and 2 were calculated in the similar manner as the example 1 except that the catalyst E-4 was used instead of the catalyst E-1 and that the coking treatment was performed at the reaction temperature of 315° C. and the LHSV of 0.1 h$^{-1}$.

Example 6

The yields of the lubricant base oil fractions 1 and 2 were calculated in the similar manner as the example 1 except that the catalyst E-2 was used instead of the catalyst E-1 and that the coking treatment was performed at the reaction temperature of 310° C. and the LHSV of 0.1 h$^{-1}$ with the reaction temperature Tc=320° C.

Example 7

The yields of the lubricant base oil fractions 1 and 2 were calculated in the similar manner as the example 1 except that the catalyst E-3 was used instead of the catalyst E-1 and that the coking treatment was performed at the reaction temperature of 315° C. and the LHSV of 0.1 h$^{-1}$.

Example 8

The yields of the lubricant base oil fractions 1 and 2 were calculated in the similar manner as the example 1 except that the catalyst E-5 was used instead of the catalyst E-1 and that the coking treatment was performed at the reaction temperature of 310° C. and the LHSV of 0.1 h$^{-1}$.

Example 9

The yields of the lubricant base oil fractions 1 and 2 were calculated in the similar manner as the example 1 except that the catalyst E-6 was used instead of the catalyst E-1 and that the coking treatment was performed at the reaction temperature of 310° C. and the LHSV of 0.1 h$^{-1}$.

Comparative Example 1

The yields of the lubricant base oil fractions 1 and 2 were calculated in the similar manner as the example 1 except that the isomerization dewaxing was started immediately after the reduction without performing coking treatment.

Comparative Example 2

The yields of the lubricant base oil fractions 1 and 2 were calculated in the similar manner as the example 6 except that the isomerization dewaxing was started immediately after the reduction without performing coking treatment.

Comparative Example 3

The yields of the lubricant base oil fractions 1 and 2 were calculated in the similar manner as the example 7 except that the isomerization dewaxing was started immediately after the reduction without performing coking treatment.

Comparative Example 4

The yields of the lubricant base oil fractions 1 and 2 were calculated in the similar manner as the example 8 except that the isomerization dewaxing was started immediately after the reduction without performing coking treatment.

TABLE 1

| | Hydro-isomerization catalyst | Volume of micropores for zeolite contained in catalyst before coking (cc/g-zeolite) | Coking treatment Temperature, °C | Coking treatment LHSV, h⁻¹ | Carbon content of catalyst after coking treatment (% by mass) | Volume of micropores per unit mass of catalyst after coking (cc/g-cat) | Volume of micropores for zeolite contained in catalyst after coking (cc/g-zeolite) | Reaction temperature Tc, °C | Yield of lubricant base oil fraction after running reaction for 10 hours (%) Fraction 1 | Yield of lubricant base oil fraction after running reaction for 10 hours (%) Fraction 2 | Yield of lubricant base oil fraction after running reaction for 100 hours (%) Fraction 1 | Yield of lubricant base oil fraction after running reaction for 100 hours (%) Fraction 2 |
|---|---|---|---|---|---|---|---|---|---|---|---|---|
| Example 1 | E-1 | 0.126 | 320 | 0.5 | 0.44 | 0.071 | 0.101 | 325 | 24 | 69 | 24 | 69 |
| Example 2 | E-1 | 0.126 | 350 | 0.5 | 0.41 | 0.081 | 0.115 | 325 | 28 | 66 | 27 | 66 |
| Example 3 | E-1 | 0.126 | 320 | 0.1 | 0.57 | 0.055 | 0.078 | 325 | 23 | 71 | 23 | 71 |
| Example 4 | E-4 | 0.079 | 320 | 0.5 | 0.69 | 0.046 | 0.065 | 325 | 23 | 70 | 22 | 72 |
| Example 5 | E-4 | 0.079 | 315 | 0.1 | 0.73 | 0.043 | 0.062 | 325 | 22 | 72 | 22 | 72 |
| Example 6 | E-2 | 0.145 | 310 | 0.1 | 0.49 | 0.069 | 0.098 | 320 | 27 | 66 | 27 | 66 |
| Example 7 | E-3 | 0.132 | 315 | 0.1 | 0.60 | 0.055 | 0.079 | 325 | 23 | 67 | 23 | 67 |
| Example 8 | E-5 | 0.130 | 310 | 0.1 | 0.50 | 0.064 | 0.092 | 325 | 26 | 67 | 26 | 67 |
| Example 9 | E-6 | 0.056 | 310 | 0.1 | 1.67 | 0.029 | 0.040 | 328 | 20 | 75 | 20 | 75 |
| Comparative example 1 | E-1 | 0.126 | Not performed | Not performed | — | — | — | 325 | 35 | 58 | 33 | 60 |
| Comparative example 2 | E-2 | 0.145 | Not performed | Not performed | — | — | — | 320 | 39 | 53 | 38 | 54 |
| Comparative example 3 | E-3 | 0.132 | Not performed | Not performed | — | — | — | 325 | 37 | 56 | 36 | 56 |
| Comparative example 4 | E-5 | 0.130 | Not performed | Not performed | — | — | — | 325 | 37 | 58 | 37 | 58 |

It was observed that in the examples 1 through 8, in which the coking treatment of the catalyst was carried out, the carbon content of the catalyst was 0.4 to 2.5% by mass, the volume of micropores per unit mass of the catalyst was 0.02 to 0.11 cc/g, and the volume of micropores per unit mass of the zeolite contained in the catalyst was 0.04 to 0.12 cc/g, the lubricant base oil fraction 2 with a sufficiently low pour point and a sufficiently high viscosity index can be produced from a petroleum slack wax at a higher yield compared to the comparative examples, in which the coking treatment was not performed.

The invention claimed is:

1. A method for producing lubricant base oil, wherein the method comprises:
   subjecting a catalyst to a coking treatment with a carbon containing compound, the coking treatment being at a temperature of 300° C. to 350° C. to obtain a hydroisomerization catalyst having a carbon content of 0.4% to 2.5% by mass, wherein the catalyst comprises a support having a one-dimensional porous structure including a 10-membered ring and at least one metal selected from the group consisting of group 8 to 10 metals of the periodic table, Mo, and W, supported on the catalyst; and
   contacting a hydrocarbon feedstock containing normal paraffins having 10 or more carbon atoms with the hydroisomerization catalyst in the presence of hydrogen at a hydroisomerization temperature of 370° C. to 450° C.

2. The method for producing lubricant base oil according to claim 1, wherein the catalyst is subjected to a coking treatment by using the hydrocarbon feedstock as the carbon-containing compound.

3. The method for producing lubricant base oil according to claim 1, wherein the hydrocarbon feedstock is further hydrofinished and vacuum-distilled after the hydrocarbon feedstock is contacted with the hydroisomerization catalyst.

4. The method for producing lubricant base oil according to claim 1, wherein the hydrocarbon feedstock is at least one selected from the group consisting of: atmospheric residues; vacuum residues; a vacuum gas oil; a slack wax; and a Fischer Tropsch synthetic wax.

5. The method for producing lubricant base oil according to claim 1, wherein the hydrocarbon feedstock includes a fraction with a boiling point at atmospheric pressure of more than 360° C.

6. The method for producing lubricant base oil according to claim 1, wherein the hydroisomerization catalyst has a volume of micropores per unit mass of the catalyst of 0.02 to 0.11 cc/g and a volume of micropores per unit mass of a zeolite contained in the catalyst of 0.04 to 0.12 cc/g.

7. The method for producing lubricant base oil according to claim 1, wherein the hydroisomerization catalyst comprises at least one zeolite selected from the group consisting of: a ZSM-22 zeolite; a ZSM-23 zeolite; an SSZ-32 zeolite; and a ZSM-48 zeolite.

8. A method for producing lubricant base oil, wherein the method comprises:
   subjecting a catalyst to a coking treatment with a carbon containing compound, the coking treatment being at a temperature of 300° C. to 350° C. to obtain a hydroisomerization catalyst having a carbon content of 0.4% to 2.5% by mass, wherein the catalyst comprises a support having a one-dimensional porous structure including a 10-membered ring and at least one metal selected from the group consisting of group 8 to 10 metals of the periodic table, Mo, and W, supported on the catalyst; and
   contacting a hydrocarbon feedstock containing normal paraffins having 10 or more carbon atoms with the hydroisomerization catalyst in the presence of hydrogen at a hydroisomerization temperature of 370° C. to 450° C., wherein the hydrocarbon feedstock includes a fraction with a boiling point at atmospheric pressure of more than 360° C.

* * * * *